US00PP24961P2

(12) United States Plant Patent
Kanaya et al.

(10) Patent No.: US PP24,961 P2
(45) Date of Patent: Oct. 7, 2014

(54) ***CALIBRACHOA* PLANT NAMED 'SUNBEL 0778'**

(50) Latin Name: ***Calibrachoa* sp.**
Varietal Denomination: Sunbel 0778

(75) Inventors: Takeshi Kanaya, Chiba (JP); Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 166 days.

(21) Appl. No.: 13/573,471

(22) Filed: Sep. 15, 2012

(51) Int. Cl.
*A01H 5/00* (2006.01)

(52) U.S. Cl.
USPC ..... Plt./413

(58) Field of Classification Search
CPC ..... A01H 5/02; A01H 5/025
USPC ..... Plt./413, 356.1
See application file for complete search history.

*Primary Examiner* — June Hwu
(74) *Attorney, Agent, or Firm* — C. A. Whealy

(57) ABSTRACT

A new and distinct cultivar of *Calibrachoa* plant named 'Sunbel 0778', characterized by its mounding plant habit; vigorous growth habit; freely branching and flowering plant habit; early and long flowering period; numerous single bright yellow-colored flowers with dull red (greyed purple) coloration towards the throat and venation; color becoming closer to dull yellowish pink (light orange red) during the summer; and good garden performance.

1 Drawing Sheet

Botanical designation: *Calibrachoa* sp.
Cultivar denomination: 'SUNBEL 0778'.

BACKGROUND OF THE INVENTION

The present invention relates to a new and distinct cultivar of *Calibrachoa* plant, botanically known as *Calibrachoa* sp. and hereinafter referred to by the name 'Sunbel 0778'.

The new *Calibrachoa* plant is a product of a planned breeding program conducted by the Inventors in Higashiomi, Shiga, Japan. The objective of the breeding program is to develop new compact, mounding and freely branching *Calibrachoa* plants with numerous attractive and uniquely colored flowers.

The new *Calibrachoa* plant originated from a cross-pollination conducted by the Inventors in Higashiomi, Shiga, Japan in April, 2008 of a proprietary selection of *Calibrachoa* sp. identified as code number 7056-2, not patented, as the female, or seed, parent with a proprietary selection of *Calibrachoa* sp. identified as code number LPY0, not patented, as the male, or pollen, parent. The new *Calibrachoa* plant was discovered and selected by the Inventors as a single flowering plant from within the progeny of the stated cross-pollination in a controlled greenhouse environment in Higashiomi, Shiga, Japan in September, 2009.

Asexual reproduction of the new *Calibrachoa* plant by vegetative cuttings in a controlled greenhouse environment in Higashiomi, Shiga, Japan since September, 2009 has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunbel 0778'. These characteristics in combination distinguish 'Sunbel 0778' as a new and distinct *Calibrachoa* plant:

1. Mounding plant habit.
2. Vigorous growth habit.
3. Freely branching and flowering plant habit.
4. Early and long flowering period.
5. Numerous single bright yellow-colored flowers with dull red (greyed purple) coloration towards the throat and venation; color becoming closer to dull yellowish pink (light orange red) during the summer.
6. Good garden performance.

Plants of the new *Calibrachoa* can be compared to plants of the female parent selection. Plants of the new *Calibrachoa* differ primarily from plants of the female parent selection in flower color as plants of the female parent selection have red purple-colored flowers. In addition, plants of the new *Calibrachoa* are more mounding than and not as upright as plants of the female parent selection.

Plants of the new *Calibrachoa* can be compared to plants of the male parent selection. Plants of the new *Calibrachoa* differ primarily from plants of the male parent selection in flower color as plants of the male parent selection have yellow-colored flowers with orange coloration towards the throat. In addition, plants of the new *Calibrachoa* are not as compact as plants of the male parent selection.

Plants of the new *Calibrachoa* can also be compared to plants of *Calibrachoa* 'Sunbelriki', disclosed in U.S. Plant Pat. No. 20,918. In side-by-side comparisons conducted in Higashiomi, Shiga, Japan, plants of the new *Calibrachoa* and 'Sunbelriki' differed primarily in the following characteristics:

1. Plants of the new *Calibrachoa* were more mounding than and not as upright to outwardly spreading as plants of 'Sunbelriki'.
2. Plants of the new *Calibrachoa* had longer internodes than plants of 'Sunbelriki'.

3. Plants of the new *Calibrachoa* had larger sepals than plants of 'Sunbelriki'.
4. Plants of the new *Calibrachoa* had lighter yellow-colored flowers than plants of 'Sunbelriki'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Sunbel 0778' grown in a container.

The photograph at the bottom of the sheet is a close-up view of a typical flowering plant of 'Sunbel 0778'.

DETAILED BOTANICAL DESCRIPTION

The aforementioned photographs and following observations, measurements and values describe plants grown in 15-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Calibrachoa* sp. 'Sunbel 0778'.

Parentage:

*Female, or seed, parent*.—Proprietary selection of *Calibrachoa* sp. identified as code number 7056-2, not patented.

*Male, or pollen, parent*.—Proprietary selection of *Calibrachoa* sp. identified as code number LPY0, not patented.

Propagation:

*Type*.—By vegetative cuttings.

*Time to initiate roots, summer*.—About one week at 15° C. to 20° C.

*Time to produce a rooted young plant, summer*.—About three weeks at 15° C. to 20° C.

*Root description*.—Fibrous; white in color.

*Rooting habit*.—Freely branching.

Plant description:

*Plant and growth habit*.—Mounding plant habit; freely branching habit with numerous lateral branches developing per plant; pinching enhances lateral branch development; vigorous growth habit.

*Plant height*.—About 18.5 cm.

*Plant diameter*.—About 39 cm.

Lateral branch description:

*Length*.—About 26.3 cm.

*Diameter*.—About 1.7 mm.

*Internode length*.—About 1.2 mm.

*Strength*.—Strong.

*Aspect*.—Upright to outwardly.

*Texture*.—Pubescent.

*Color*.—Close to N144C.

Foliage description:

*Arrangement*.—Alternate, simple.

*Length*.—About 4.1 cm.

*Width*.—About 1.2 cm.

*Shape*.—Oblanceolate.

*Apex*.—Acute.

*Base*.—Cuneate.

*Margin*.—Entire.

*Texture, upper and lower surfaces*.—Pubescent.

*Venation pattern*.—Pinnate; reticulate.

*Color*.—Developing leaves, upper surface: Close to 143B. Developing leaves, lower surface: Close to 143C. Fully expanded leaves, upper surface: Close to 146A; venation, close to 145A. Fully expanded leaves, lower surface: Close to 146B; venation, close to 145B.

*Petiole*.—Length: About 3.4 mm. Diameter: About 0.4 mm. Texture, upper and lower surfaces: Pubescent. Color, upper and lower surfaces: Close to 144C.

Flower description:

*Flower arrangement and habit*.—Single salverform flowers arising from upper leaf axils; freely flowering habit with usually about 32 flowers developing per plant; flowers face upright or outwardly.

*Fragrance*.—None detected.

*Natural flowering season*.—Early flowering habit, plants of the new *Calibrachoa* initiate and develop flowers about three to four weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower diameter*.—About 3.3 cm.

*Flower length (depth)*.—About 2.4 cm.

*Throat diameter*.—About 7.8 mm.

*Tube length*.—About 1.6 cm.

*Tube diameter, base*.—About 2.2 mm.

*Flower bud*.—Shape: Cylindrical. Length: About 2.3 cm. Diameter: About 5.9 mm. Color: Close to 2B; venation, close to 178B.

*Corolla*.—Arrangement: Five petals fused at the base and opening into a flared trumpet. Petal length from throat: About 1.2 cm. Petal width: About 1.4 cm. Petal shape: Spatulate. Petal apex: Rounded. Petal margin: Entire. Petal texture, upper and lower surfaces: Smooth, glabrous. Throat texture: Smooth, glabrous. Tube texture: Pubescent. Color: Petal, when opening and fully opened, upper surface: Close to 2A; towards the throat, close to 184A; venation, close to 184A; during the summer, color becoming closer to 35C. Petal, when opening and fully opened, lower surface: Close to 8C; venation, close to 178B. Throat: Close to 2A; venation, close to N187A. Tube: Close to 8C; venation, close to 187A.

*Calyx*.—Arrangement: One star-shaped tubular calyx tube with five sepals fused at the base. Sepal length: About 1.3 cm to 1.9 cm. Sepal width: About 4.4 mm. Sepal shape: Lanceolate. Sepal apex: Acute. Sepal margin: Entire. Sepal texture, upper and lower surfaces: Pubescent. Sepal color: Immature and mature, upper surface: Close to 137C. Immature and mature, lower surface: Close to 137D.

*Peduncles*.—Length: About 2.2 cm. Diameter: About 0.8 mm. Angle: Semi-upright. Strength: Strong. Texture: Pubescent. Color: Close to 144A.

*Reproductive organs*.—Stamens: Quantity: Five per flower. Stamen length: About 9 mm to 12 mm. Anther shape: Ellipsoidal. Anther size: About 1.7 mm by 1.4 mm. Anther color: Close to 1A. Pollen amount: Moderate. Pollen color: Close to 2B. Pistils: Quantity: One per flower. Pistil length: About 9.7 mm. Style color: Close to 144D. Stigma shape: Transversely ellipsoidal. Stigma color: Close to 144B. Ovary color: Close to 144B.

*Seeds and fruits*.—Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen & pest resistance: Plants of the new *Calibrachoa* have not been observed to be resistant to pests and pathogens common to *Calibrachoa* plants.

It is claimed:

1. A new and distinct *Calibrachoa* plant named 'Sunbel 0778' as illustrated and described.

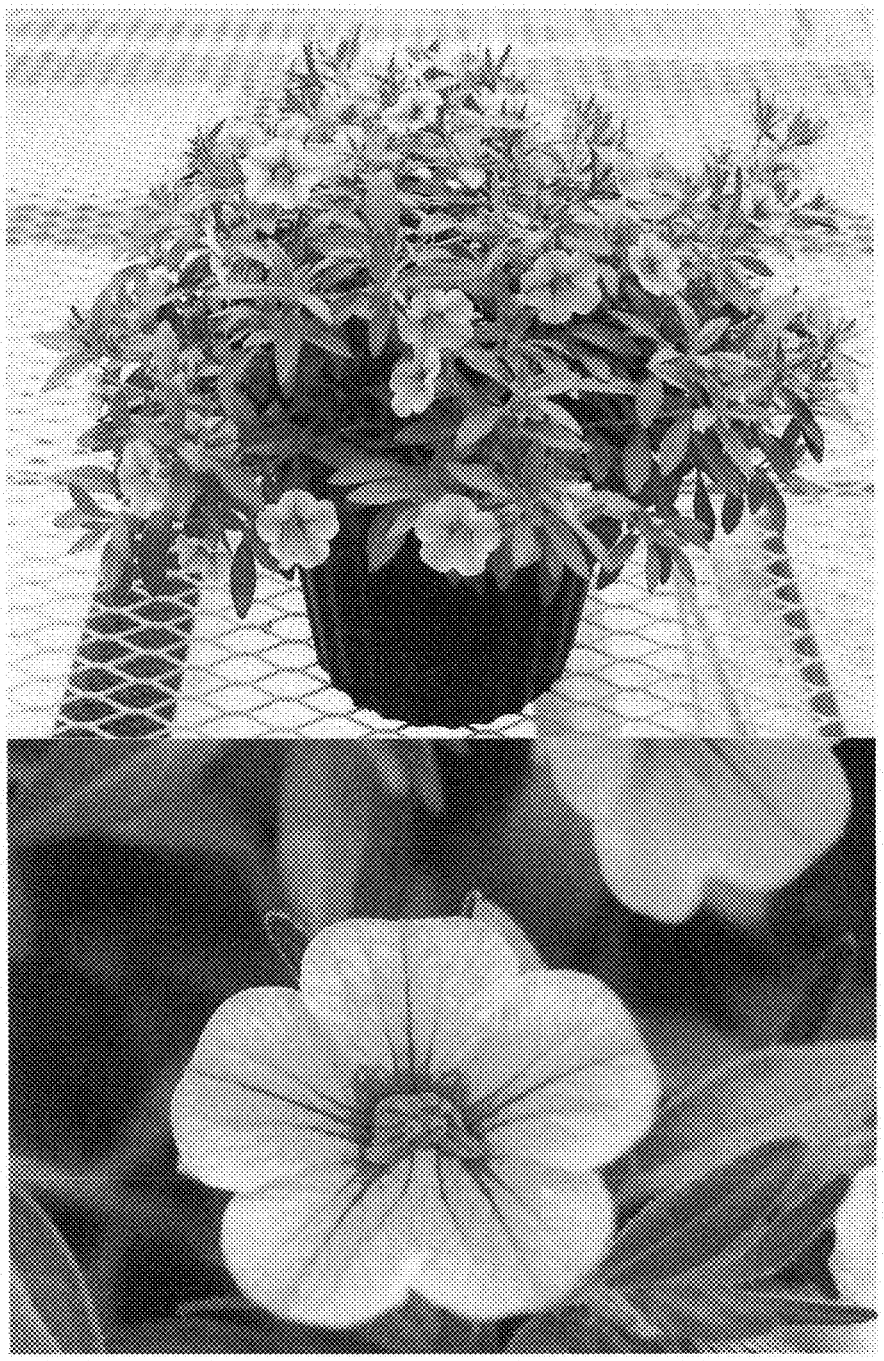

* * * * *